United States Patent [19]
Dillman et al.

[11] 3,953,848
[45] Apr. 27, 1976

[54] ELECTROCARDIOGRAPH TELEMETRY SYSTEM INCLUDING METHOD AND MEANS FOR INDICATING INOPERATIVE CONDITIONS

[75] Inventors: Richard F. Dillman, Lexington; James L. Larsen, Bedford; Alfred M. Nardizzi, Dedham, all of Mass.

[73] Assignee: Hewlett-Packard Company, Palo Alto, Calif.

[22] Filed: Apr. 12, 1974

[21] Appl. No.: 460,629

Related U.S. Application Data
[62] Division of Ser. No. 373,552, June 25, 1973, Pat. No. 3,829,782, which is a division of Ser. No. 207,859, Dec. 14, 1971, Pat. No. 3,768,017.

[52] U.S. Cl. .......................... 340/409; 128/2.06 R; 128/2.1 A; 340/253 Y; 340/279; 325/48; 325/186
[51] Int. Cl.² ..................... G08B 29/00; A61B 5/04
[58] Field of Search .......... 340/180, 181, 186, 409, 340/207 R, 208, 177 CA, 279, 253 Y; 324/58 A; 128/2.05 R, 2.06 R, 2.1 A

[56] References Cited
UNITED STATES PATENTS

| | | | |
|---|---|---|---|
| 3,212,496 | 10/1965 | Preston | 128/2.06 |
| 3,253,588 | 5/1966 | Vuilleumier et al. | 128/2 |
| 3,631,433 | 12/1971 | Dix | 340/216 |
| 3,639,907 | 2/1972 | Greatbatch | 340/150 |
| 3,641,547 | 2/1972 | Reiss et al. | 340/253 R |

*Primary Examiner*—John W. Caldwell
*Assistant Examiner*—James J. Groody
*Attorney, Agent, or Firm*—A. C. Smith

[57] ABSTRACT

Special circuitry in the transmitter of an electrocardiograph (ECG) telemetry system detects various malfunctions of the system and changes the transmitted signal to indicate their presence to the system receiver. When the transmitter detects that an input electrode has become detached from the patient, it changes the frequency of the subcarrier signal to indicate this problem to the receiver. The receiver monitors the subcarrier frequency and flashes an alarm light when the frequency corresponds to the electrode inoperative condition.

2 Claims, 15 Drawing Figures

ELECTROCARDIOGRAPH TELEMETRY SYSTEM INCLUDING METHOD AND MEANS FOR INDICATING INOPERATIVE CONDITIONS

CROSS-REFERENCE TO RELATED APPLICATION

This is a divisional application of U.S. application Ser. No. 373,552 filed on June 25, 1973, by Richard F. Dillman, James L. Larsen and Alfred M. Nardizzi, now U.S. Pat. No. 3,829,782, which is a divisional application of U.S. application Ser. No. 207,859 filed on Dec. 14, 1971, by Richard F. Dillman, James L. Larsen and Alfred M. Nardizzi, now U.S. Pat. No. 3,768,017.

BACKGROUND OF THE INVENTION

A patient recovering from heart surgery or suffering a myocardial infarction must be kept under constant observation until his heart condition improves. Monitoring the electrocardiac signals, sometimes called ECG signals, produced by the expansions and contractions of the patient's heart is a common method of observation during this time. These electrocardiac signals are present on the skin and throughout the body. They are a valuable medical indicator because their shape and repetition rate can indicate to a trained observer whether the heart is operating properly or nearing a dangerous condition.

During the initial phase of a heart patient's recovery, he is bedridden and directly connected to a bedside monitor, such as an electrocardiograph. The monitor is usually wired to electrodes that are attached to the skin near the heart. The electrodes detect the electrocardiac signals that are circulating on the skin, and the wires transmit them to the monitor.

When a patient's condition improves, it is often desirable to let him move about. This is difficult if he remains connected to the bedside monitor because the wires restrict his movement. To remedy this problem, a telemetry system is sometimes used to replace the direct wired connection.

The telemetry system includes a portable transmitter carried by the ambulatory patient and a stationary receiver connected to the monitor. Electrodes still sense the electrocardiac signals, but now the signals are transmitted by radio waves to the receiver. At the receiver, the transmitted signal is demodulated and the resultant electrocardiac signal is conveyed to the monitor. With such a telemetry system, a heart patient can move about while his electrocardiac signals are kept under constant surveillance.

If a heart monitoring system becomes inoperative, a special indication should be given to the monitor operator so that the fault can be quickly corrected and so that the inoperative condition will not result in confusion and create a false heart rate alarm. Because of the increased movement of an ambulatory patient, there are more problems involved with a telemetry monitoring system than with a stationary monitor. Patient movement may disconnect an electrode, stopping detection of the electrocardiac signals, or it may shift the position of an electrode, weakening the detected ECG signals. An ambulatory patient may also move out of the range of the receiver and ruin the reception.

SUMMARY OF THE INVENTION

The present invention detects various inoperative conditions that are common to ECG telemetry systems, and it indicates to the system operator that these conditions exist. It also inhibits the receiver output when an inoperative condition is detected to prevent the output of erroneous ECG signals to the monitor.

This invention monitors the input signal to the transmitter to detect when an electrode detaches from the patient's skin or when the input wires develop an open circuit. When such a condition is detected, the subcarrier frequency of the transmitted signal is changed by special circuitry in the transmitter. The receiver is designed to detect this frequency change and light an alarm light to signal the problem to the operator.

DESCRIPTION OF THE DRAWINGS

FIGS. 2(A-H) are portions of the composite schematic diagram showing the circuit configuration of the transmitter including the input circuitry that detects an open circuit at the input terminals.

DESCRIPTION OF THE PREFERRED EMBODIMENT

Figure 1:
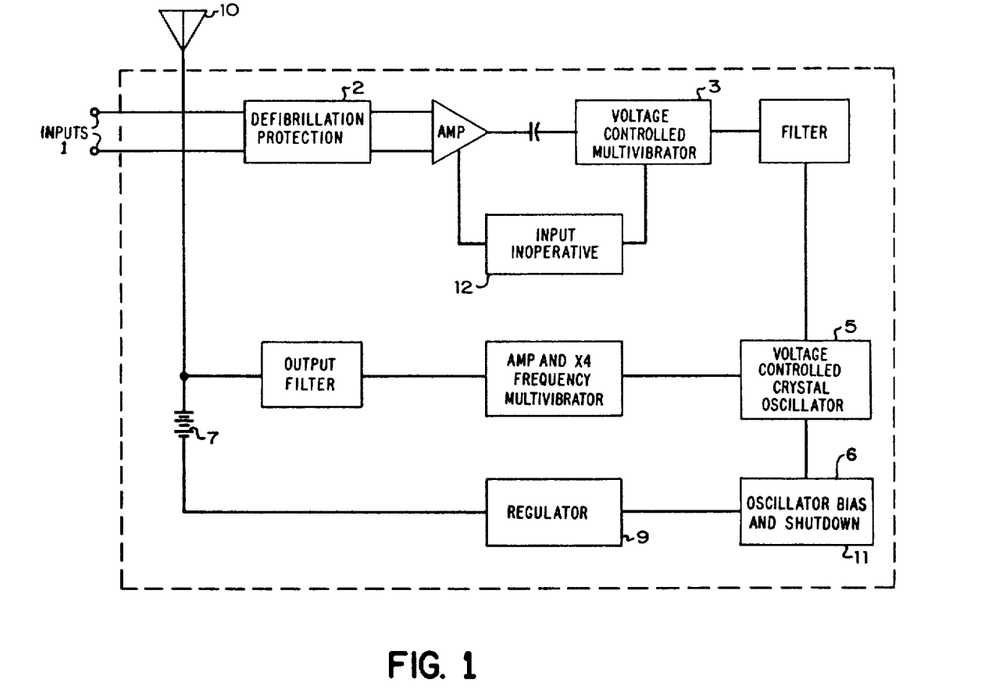
FIG. 1 is a block diagram showing the preferred embodiment of the inoperative circuitry in a conventional transmitter.
Figure 2:
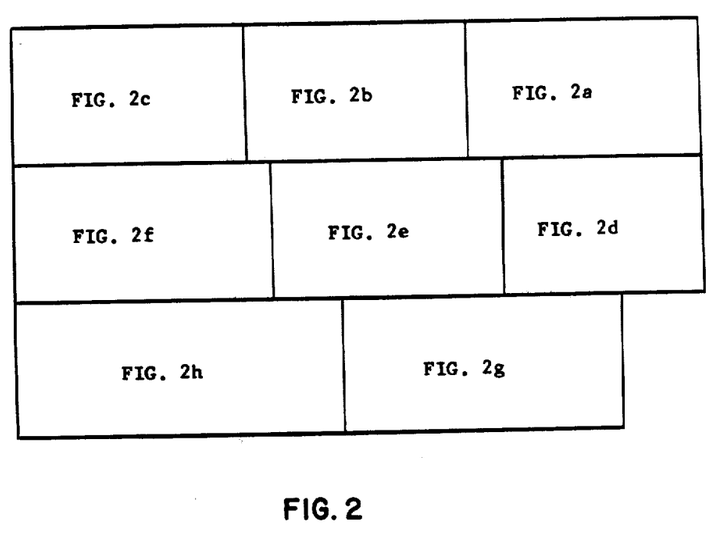
FIG. 2 is a block diagram showing the diagrammatic positions of FIGS. 2 (A-H).

Referring now to FIGS. 1 and 2 and 2(A-H), two input terminals 1 are connected to sensing electrodes that are attached to a patient to pick up his ECG signals. The input terminals are connected to circuitry 2 that protects the transmitter from damage by the high voltages used in defibrillation. After passing through an amplifier, the ECG signals are used to frequency modulate a subcarrier signal generated by the voltage controlled multivibrator 3. After the modulated subcarrier is filtered, it is used to frequency modulate a carrier signal generated by the voltage controlled crystal oscillator 5. The resulting FM—FM signal is multiplied in frequency by a factor of 4, is filtered, and is then transmitted from the antenna 10. A power supply 7 and a regulator 9 provide the energy to operate the transmitter. Since the transmitter must be portable, the power supply is usually a battery.

If an input electrode becomes detached from the patient, or if one of the inputs develops an open circuit, the input inoperative circuitry 12 detects the condition and reduces the subcarrier frequency to signal this inoperative condition to the receiver. The circuitry detects the open condition by sensing the unusually low input current associated with an open circuit.

Figure 2A:
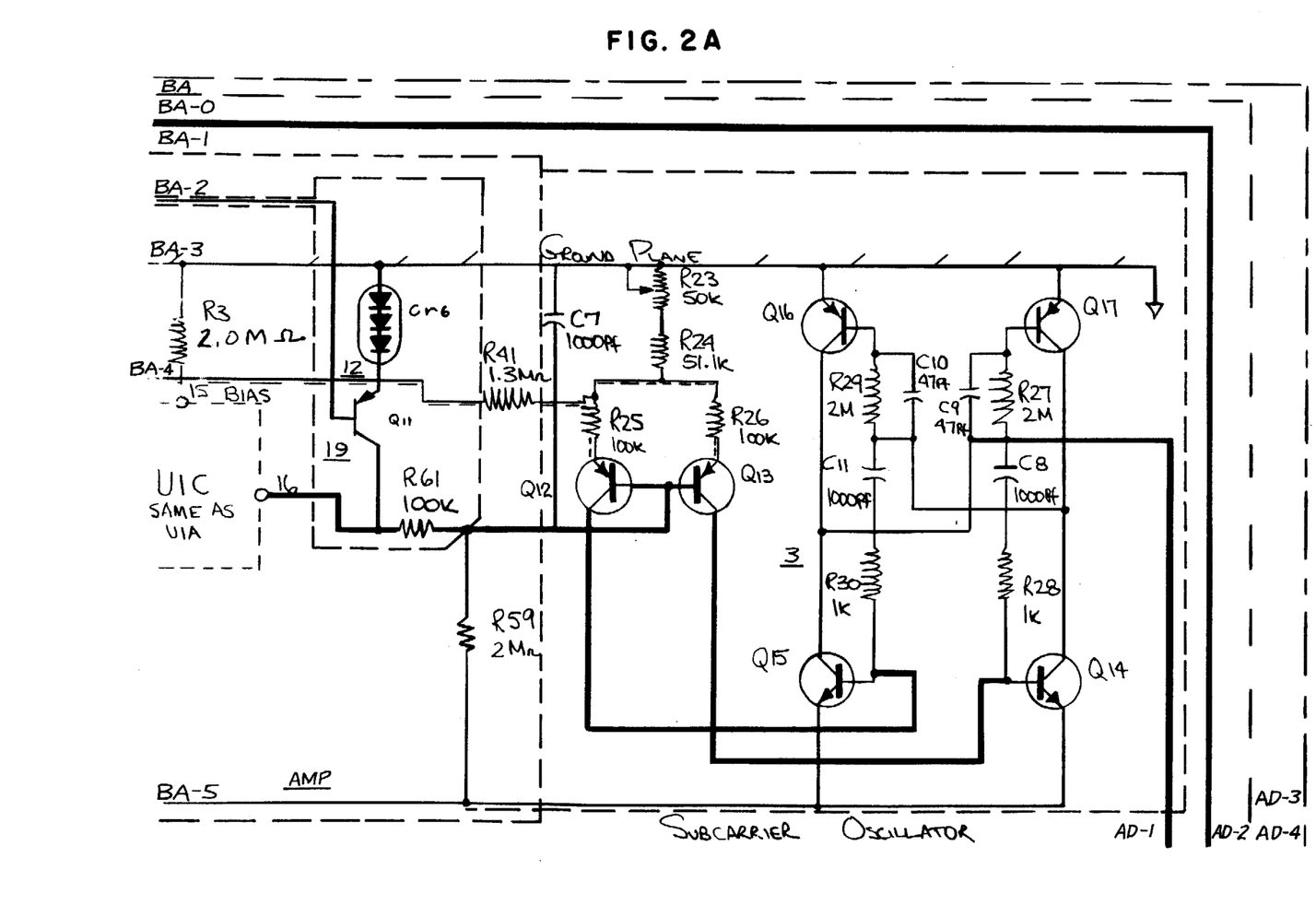
Figure 2B:
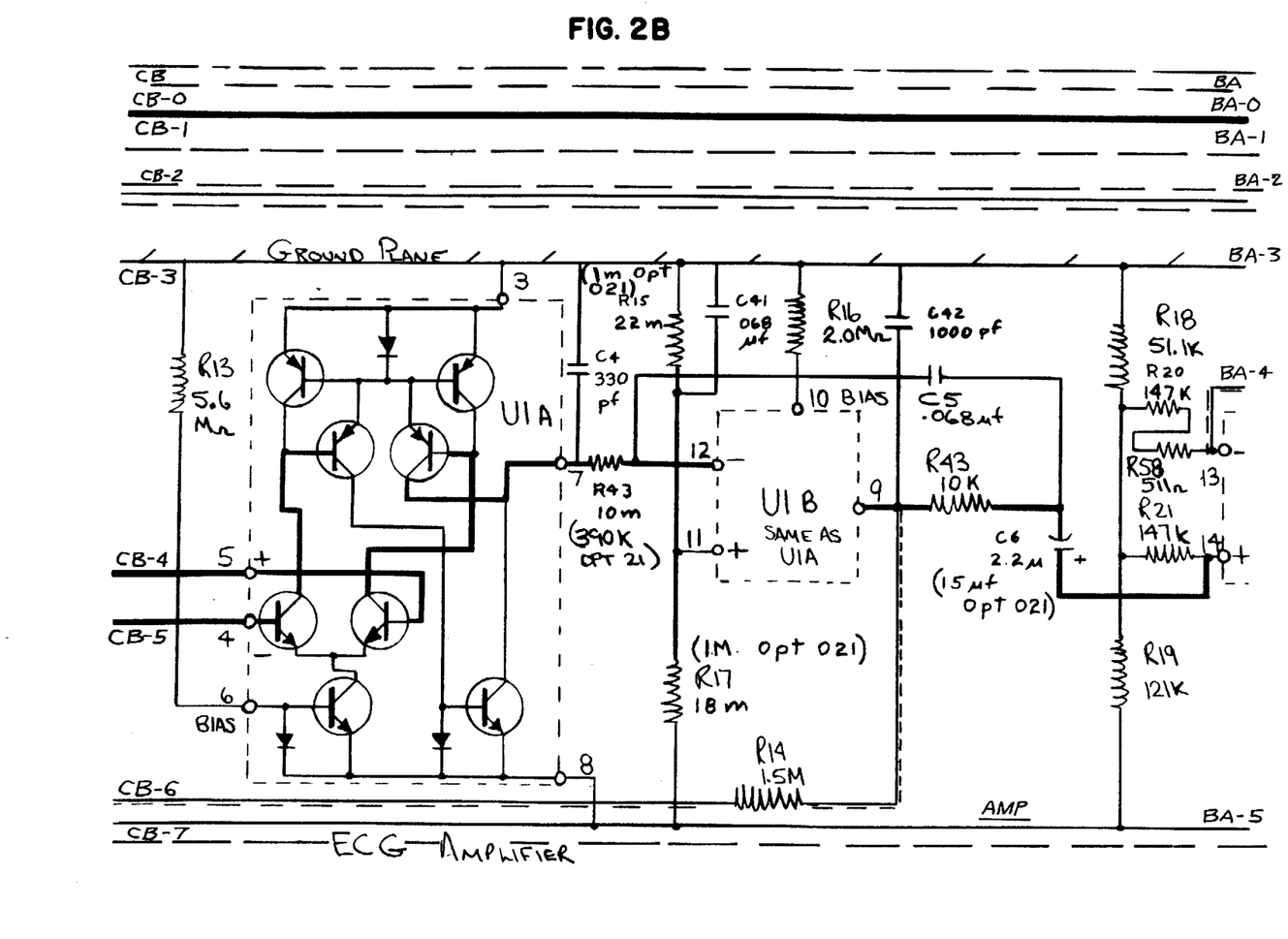
Figure 2C:
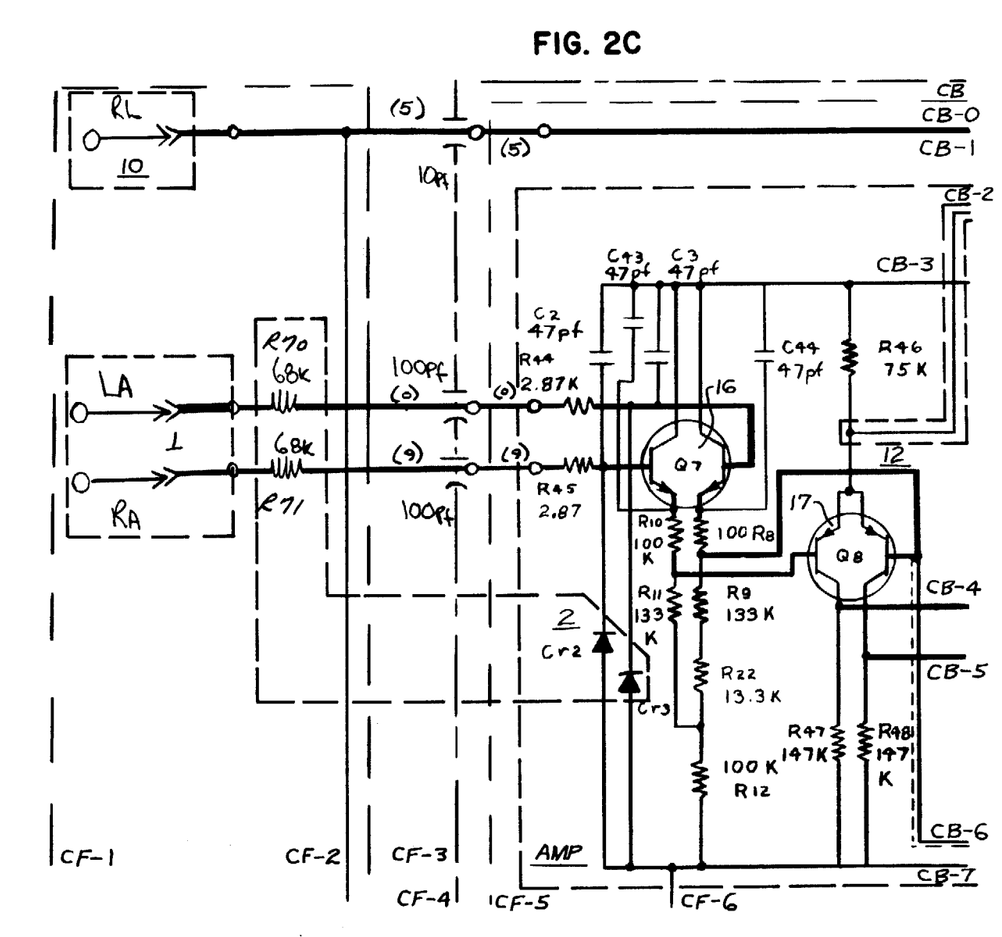
Figure 2D:
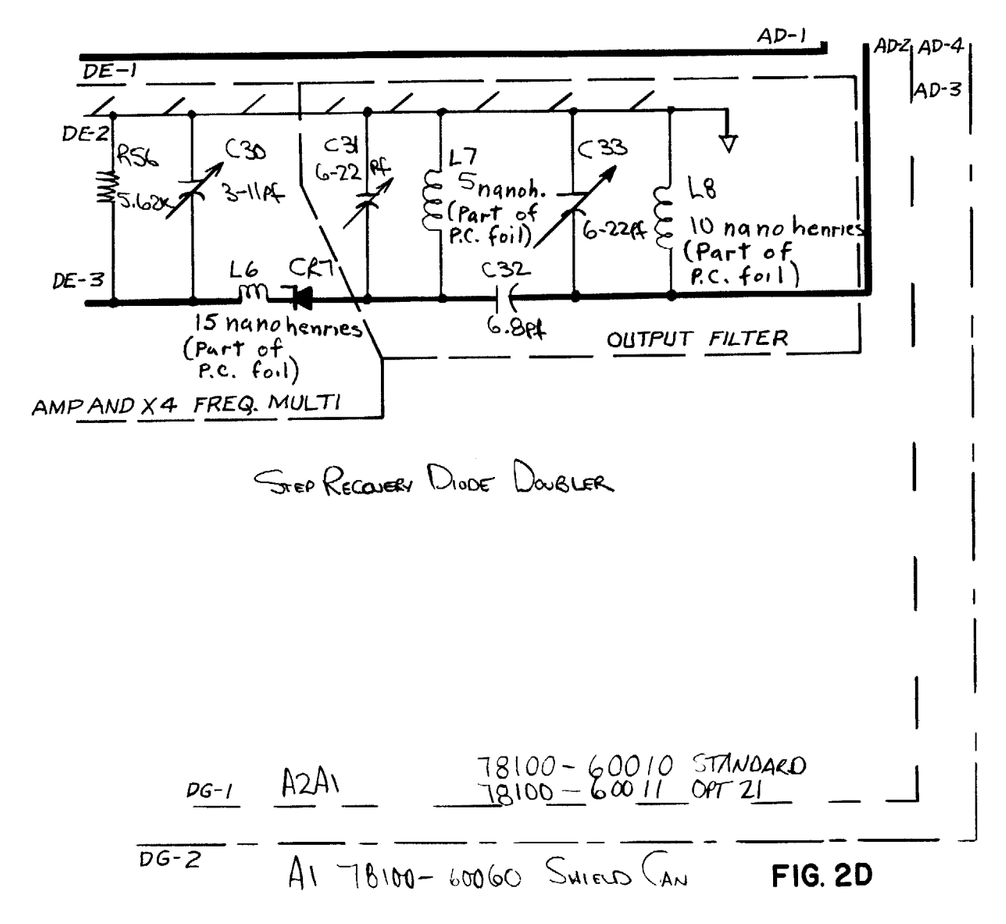
Figure 2E:
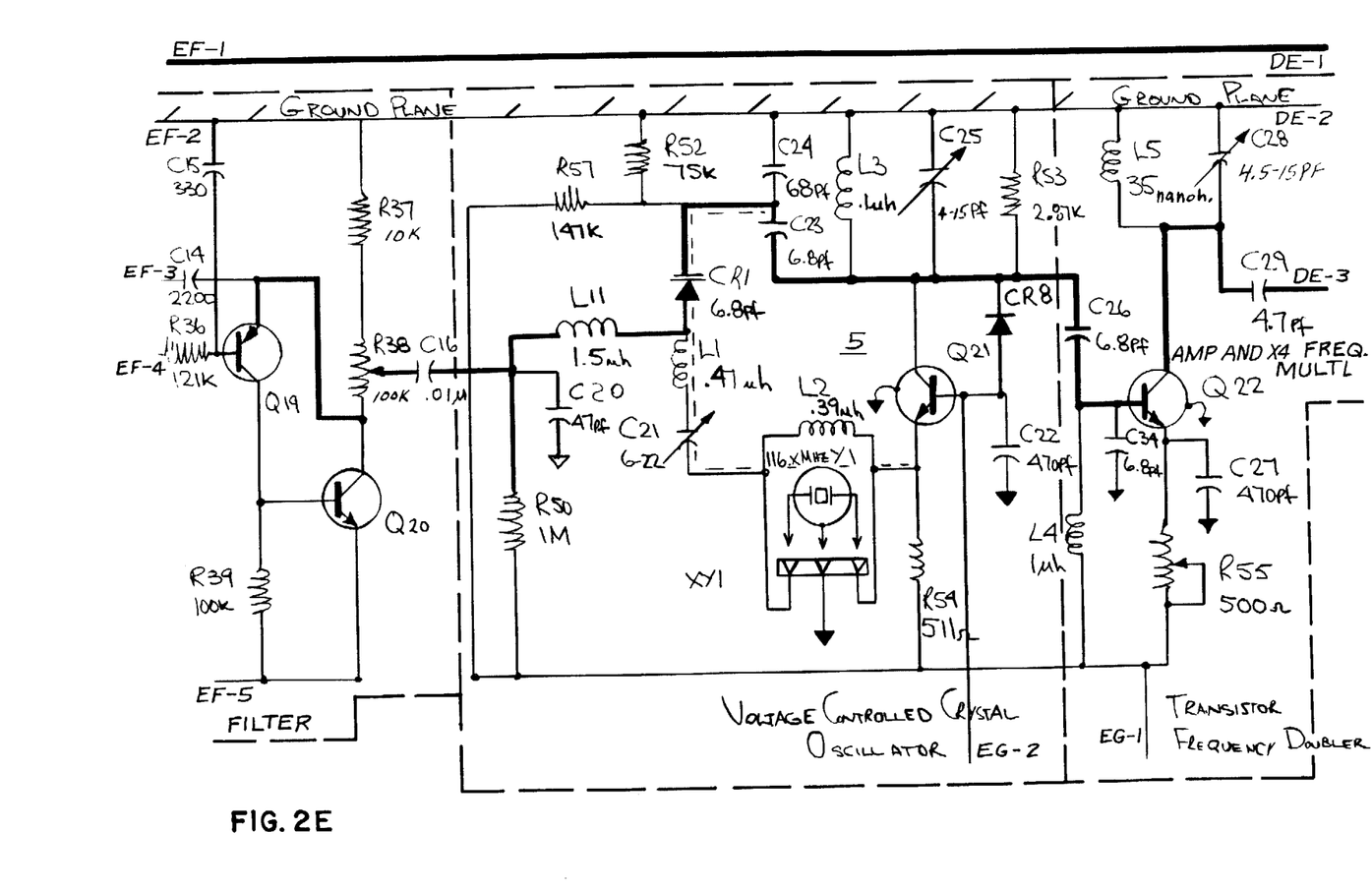
Figure 2F:
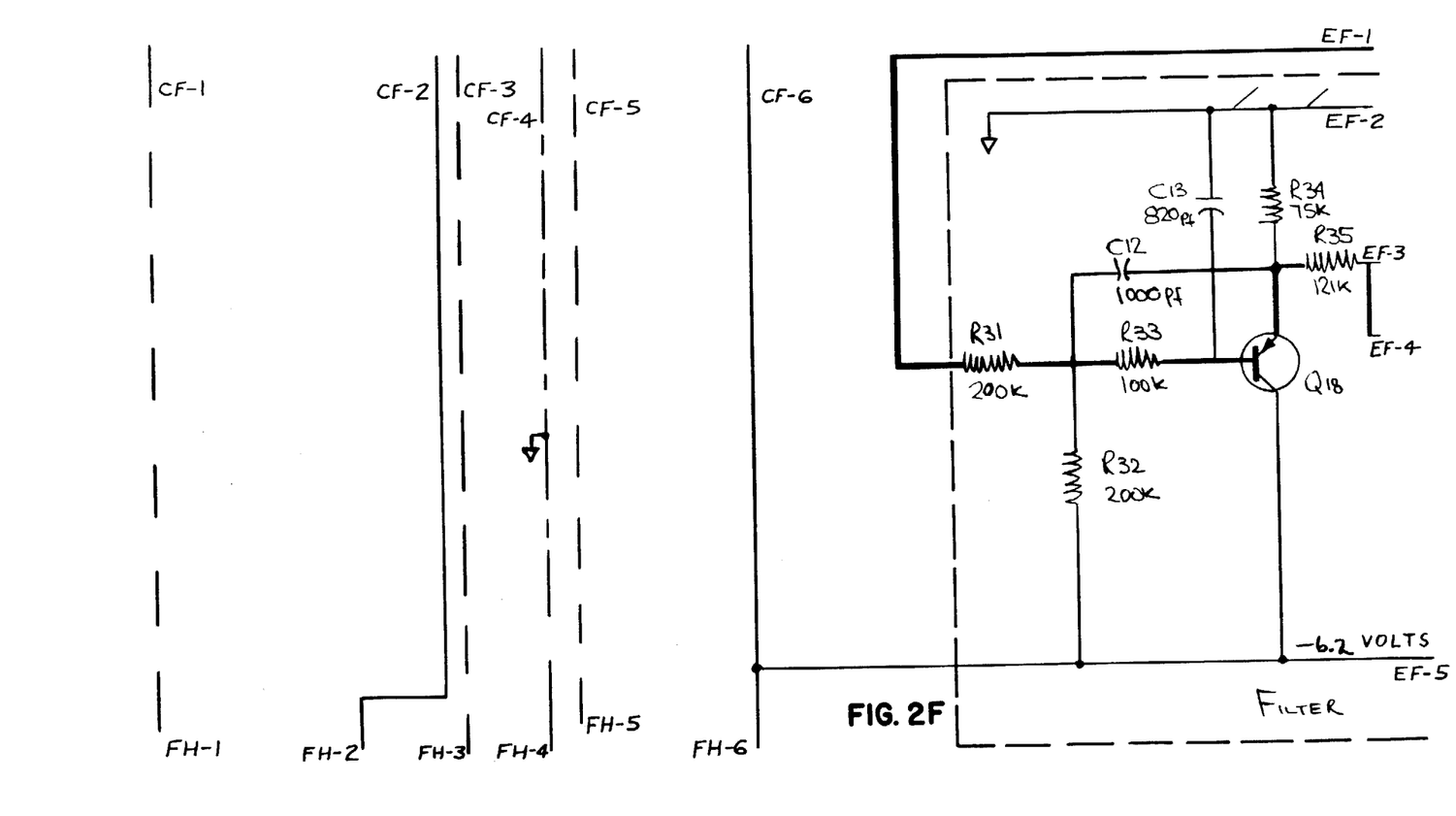
Figure 2G:
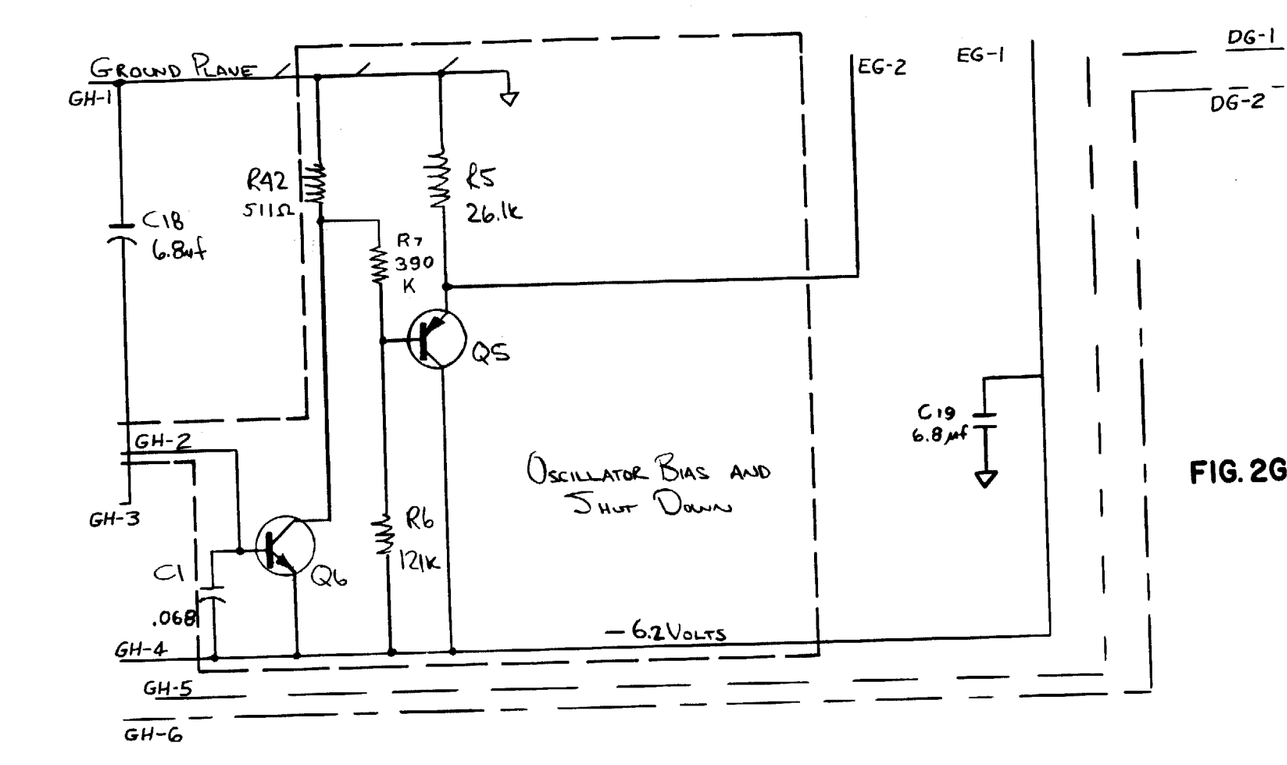
Figure 2H:
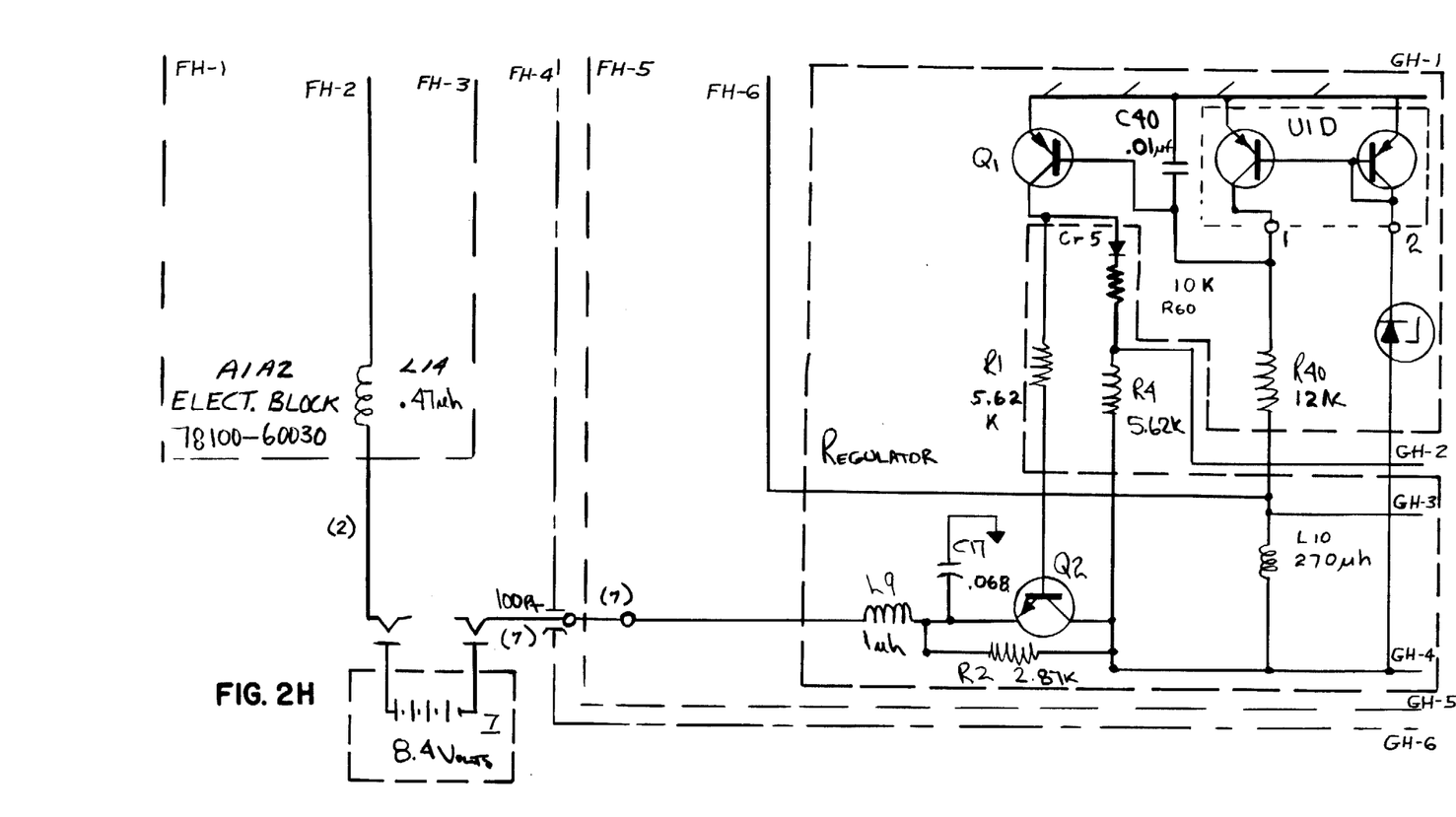

Referring now to the schematic diagram of FIG. 2C which shows the input inoperative circuitry, a detached electrode causes the signal at one of the inputs 1 to float towards the voltage level of the supply 20. This will shut off the corresponding transistor of the transistor pair 16. This, in turn, will saturate the corresponding transistor of the transistor pair 17. The saturated transistor will draw an increased current through resistor 18 and increase the emitter-base voltage of transistor 19. This will turn on transistor 19 which is normally off. The collector of transistor 19 is connected to a voltage divider that controls the output frequency of the voltage controlled multivibrator 3, as shown in FIG. 2A.

The output frequency of a voltage controlled multivibrator, a device well known in the art, is dependent on the input voltage. Transistor 19 and its output voltage divider are constructed to decrease the frequency of the multivibrator to approximately one half or less of its normal frequency. Since this is the subcarrier signal, the input inoperative signal is transmitted to the receiver by the decrease in the subcarrier frequency. Circuitry in the receiver will detect this frequency change and indicate the input inoperative condition.

The carrier oscillator includes a single bipolar transistor $Q_{21}$ connected in a common base configuration. The collector of transistor $Q_{21}$ is turned by the resonant circuit of capacitor $C_{25}$ and inductor $L_3$ to maximize the power gain of the stage at the desired frequency. Positive feedback to sustain oscillations is provided by the capacitive divider formed of capacitors $C_{23}$ and $C_{24}$, and by the feedback path including varactor diode $CR_1$, inductor $L_1$, capacitor $C_{21}$, and crystal resonator $Y_1$ connected to the emitter of transistor $Q_{21}$. Capacitor $C_{22}$ is a signal bypass and the frequency of oscillation is determined primarily by the crystal $Y_1$.

Experimental tests indicate that spurious oscillations are generated by the saturation of the collector-base junction of $Q_{21}$ under normal operating conditions. This junction of the transistor is shunted by a metal-semiconductor Schottky-barrier type diode $CR_8$ that has lower saturation voltage than that of the collector-base junction to prevent saturation with concomitant generation of spurious frequencies. This simplifies the transmitter circuitry by reducing the filtering requirements and also greatly facilitates the tuning-up procedures required to establish proper operation on the assigned frequency.

Referring again to FIGS. 1 and 2 and 2(A–H), the oscillator bias and shut down circuitry 11 detects a low battery supply 7. A weak battery causes the regulator 9 to become ineffective, and signals generated during this condition may be erroneous because of supply voltage drift. The regulator includes a series-pass transistor, a device well known in the art. As the battery output current decreases, the voltage drop across the emitter-collector terminals of the series-pass transistor decreases. This causes the transistor to begin to saturate and draw more base current. When the transistor saturates, the regulator loses control over the output of the voltage supply.

To detect this problem, the oscillator shut down circuitry 11 monitors the base current in the series-pass transistor. When the current exceeds a given value, the shut down circuitry prevents the generation of the carrier signal and stops the radiation from the transmitter. In the process of the transistor 6 turning on to prevent the oscillator from operating, it draws more current than is normally supplied to the oscillator, thus further reducing battery voltage and assuring that the oscillator remains locked off. Without this current drain to replace the oscillator current drain, the reduced current drain on the battery would result in increased battery voltage sufficient to reactivate the oscillator. This would produce an unstable condition that would result in intermittent transmission. The present circuit thus assures that the transmission of erroneous signals due to an unregulated power supply is prevented.

Figure 3:
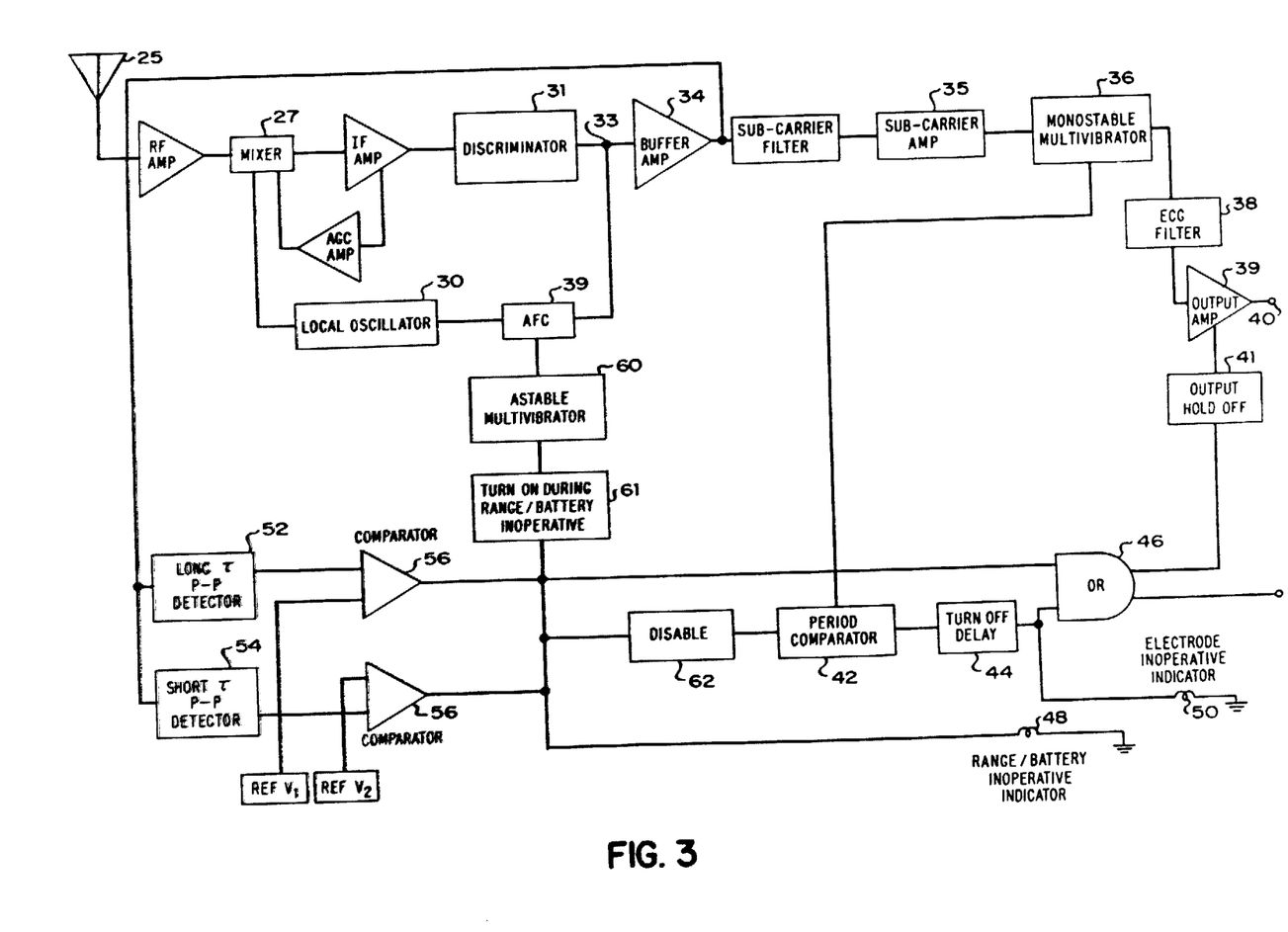
FIG. 3 is a block diagram showing the preferred embodiment of the inoperative circuitry in the receiver.

Referring now to FIG. 3, wherein is shown a functional diagram of the receiver circuitry, the FM—FM signal transmitted from the ambulatory patient is received at the antenna 25 of the stationary receiver. After amplification, this signal is demodulated to an IF signal in the conventional manner. It is frequency mixed at the mixer 27 with a local oscillator signal which is generated by the local oscillator 30. After passing through the discriminator, the resultant signal at node 33 is the frequency modulated subcarrier signal carrying the ECG information.

After passing through a buffer amplifier and a filter, the signal is converted from a sinusoid to a square wave by the subcarrier amplifier 35. The square wave then drives a monostable multivibrator 36 that gives a pulse output for every positive or negative transition of the square wave. The multivibrator output carries the ECG signal in its frequency modulated pulse train. The pulse train is time averaged and filtered by the ECG filter 38, and the filter output is the original ECG signal detected by the electrodes attached to the patient. This signal is amplified by the output amplifier 39. The output terminal 40 can be connected to an electrocardiograph or any other appropriate monitoring device. Thus, the receiver performs two demodulations of the FM—FM input signal to extract the original ECG signal.

The receiver detects a detached electrode by monitoring the frequency of the subcarrier signal. Since the pulse output from the multivibrator 36 is directly proportional to the ECG modulated subcarrier, the receiver compares the period between the pulse to a predetermined period. This is done by the period comparator 42 that is connected to an output from the multivibrator. The pulse output is used to discharge a capacitor. When there is no pulse, the capacitor charges. Consequently, for lower frequencies, i.e. longer periods between pulses, the capacitor charges to higher voltages. For a low enough frequency, the capacitor charges to a voltage high enough to trigger the electrode inoperative circuitry.

The period comparator is adjusted to trigger the turn-off delay 44 when the pulse train frequency corresponds to a subcarrier frequency indicative of the electrode inoperative condition. For the transmitter shown in FIG. 1, the comparator would be set to trigger when the subcarrier is at one-half its normal frequency, which is outside the normal operating band of frequencies. The turn-off delay energizes the electrode inoperative indicator 50 to signal to the operator that this problem exists. The turn-off delay also shuts down the output from the receiver by energizing the output hold off circuitry 41. This is done to prevent erroneous output signals.

The receiver senses the signal conditions that indicate when the patient is out of range or when the transmitter is inoperative. This sensing circuitry includes two peak-to-peak detectors 52, 54 connected to the output of the buffer amplifier 34 and a window comparator 56 that examines the output from the detectors. The comparator drives circuitry 60, 61 that controls the local oscillator frequency. It also controls the output hold off circuitry 41 and the range/battery inoperative indicator 48. When the window comparator detects an inoperative condition, it disables the electrode inoperative circuitry 42, 44 to prevent erroneous indications of detached electrodes.

The input to the peak-to-peak detectors 52, 54 is the ECG modulated subcarrier signal. These detectors, well known in the art, convert the peak-to-peak voltage of the FM subcarrier signal to a representative D.C. voltage. One detector 52 holds the peak-to-peak voltage for a relatively long time while the other detector 54 holds the voltage for a much shorter time. Each detector includes two capacitors that charge respectively to the peak voltage of the negative half cycle and the peak-to-peak voltage excursion. The period of measurement of a detector is determined by the discharge times of the capacitors.

Figure 4:
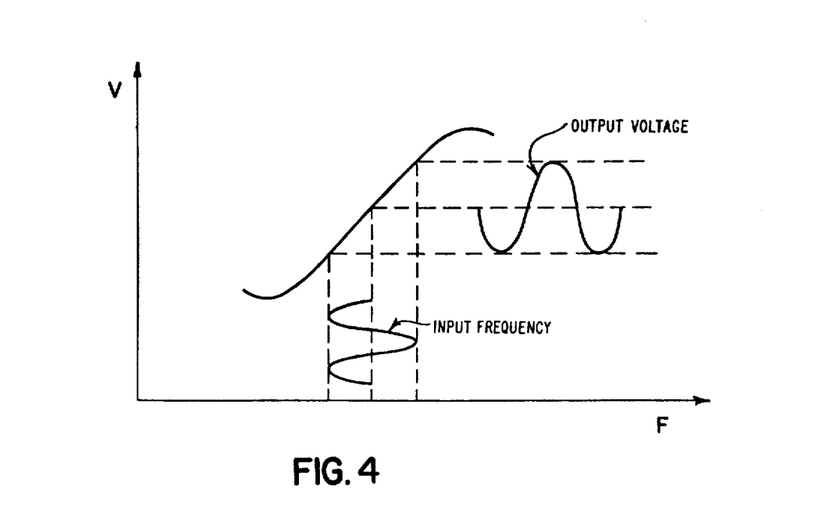
FIG. 4 is a graphical diagram showing the transfer characteristics of a frequency discriminator.
Figure 5:
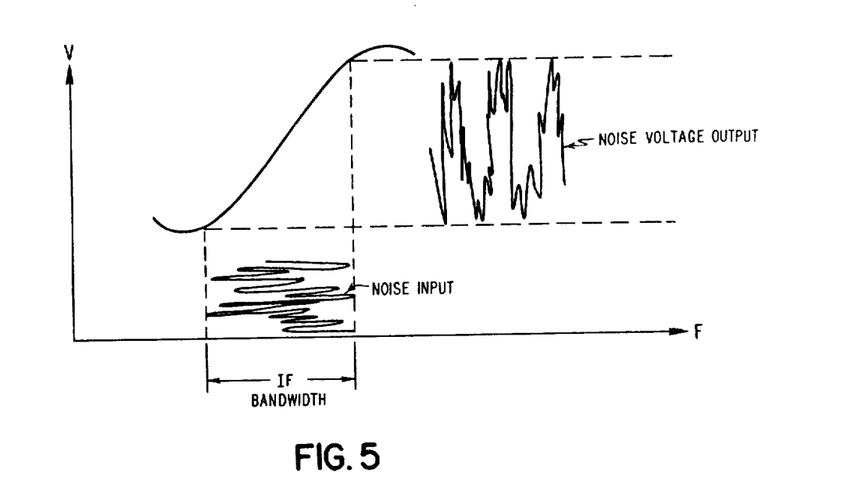
FIG. 5 is a graphical diagram showing the noise output voltage of the frequency discriminator.

The range/battery inoperative detection may be considered as working on the amplitude of the demodulated subcarrier. The output of an FM discriminator is a wave having an amplitude that is related to the frequency deviation of the carrier, as shown in FIG. 4. The discriminator output for a noise input signal thus typically has a higher peak amplitude and, for interference input signals, may generally have either higher or lower peak amplitude than on applied input signals, as shown in FIG. 5. As an example, consider an AM signal as an interference signal applied to the frequency discriminator. Since the carrier frequency does not deviate with time, the discriminator output may be simply a static value that can be readily analyzed.

Figure 6:
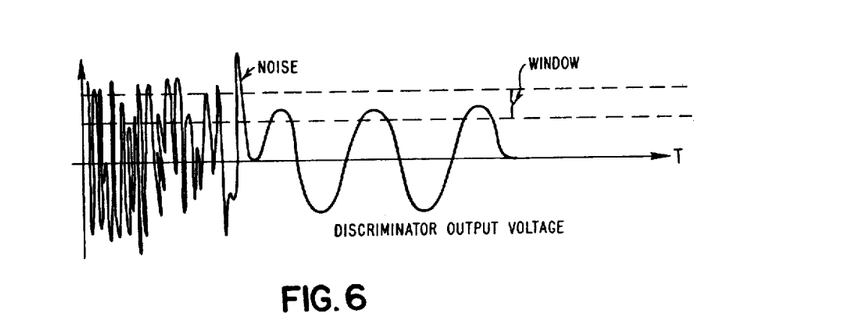
FIG. 6 is a graphical diagram showing the operation of comparators on the output of a frequency discriminator.
Figure 7:
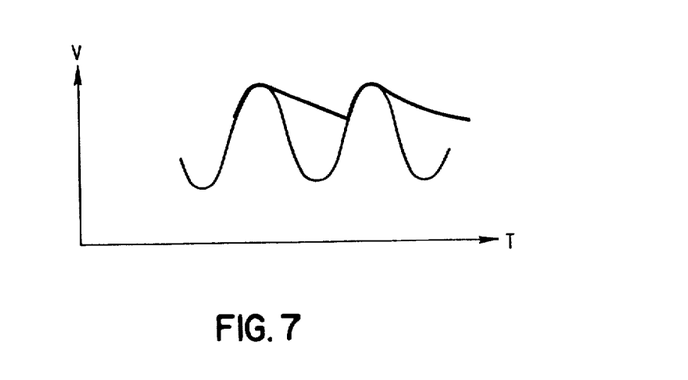
FIG. 7 is a graphical diagram showing the charging characteristics of the detector circuits.

By using the comparators 56 and 56', it is possible to set a narrow "window" about the discriminator output voltage and require that the peak output amplitude remain in the "window" selectively, as shown in FIG. 6, to unlock the inoperative circuits. The time constants of the detectors 52, 54 may be chosen such that for transitions between noise and interference, there is no interim period where the inoperative circuits unlock, i.e., one comparator would be activated before the other comparator releases. The detectors charge quickly on output signal and discharge at the selected time-constant rate, as shown in FIG. 7.

Referring again to FIG. 3, the upper limit of comparator 56 of conventional design is set to trigger on amplitudes above the ECG modulated subcarrier amplitudes. These higher amplitude signals are caused by noise received by the antenna when the transmitter is out of range or no longer transmitting. The latter occurs when the low battery circuit in the transmitter shuts down transmission. When the output of the longer time constant detector 52 reaches a voltage higher than a reference voltage that corresponds to the upper trigger amplitude, the comparator energizes the range/battery inoperative indicator 48.

The lower limit of the comparator 56' is set to trigger on amplitudes below the ECG modulated subcarrier amplitude. These lower amplitude signals result from an unmodulated or off channel interfering frequency. When the output of the shorter time-constant detector 54 decreases to a voltage below a reference voltage that corresponds to the lower trigger voltage, the comparator 56' energizes the range/battery inoperative indicator 48. Thus the window comparator 56 is unresponsive to signals within its "window", but for signals above or below set limits, it energizes the range/battery inoperative circuitry.

Beside energizing the inoperative indicator 48, the comparator triggers the output hold off circuitry 41 when it detects an inoperative condition. The hold off grounds the output terminal 40 to prevent an erroneous output from the receiver. The comparator also disables the electrode inoperative circuitry 42, 44, 50 to prevent an erroneous indication of a detached electrode when there is a range/battery inoperative condition.

The window comparator is connected to the local oscillator loop in the demodulation circuitry. The comparator output controls the automatic frequency control (AFC) 39 to regulate the local oscillator frequency. When the comparator detects an inoperative condition, it energizes the free running multivibrator 60. The multivibrator varies the local oscillator frequency from near one band edge and then releases it to the control of the AFC loop. If the inoperative circuit does not clear, the multivibrator then sets the local oscillator to a frequency near the other band edge and releases it to the control of the AFC loop. This action continues until the receiver locks on an appropriate received signal. When a transmitted signal is received and detected, the range/battery inoperative circuitry 41, 60, 61, 62 and the indicator 48 will turn off. Then the receiver will operate normally.

As shown, this invention detects and indicates certain malfunctions of an ECG telemetry system. Accurate detection and prompt indication of malfunctions are invaluable to ECG monitoring systems because they permit continual monitoring of the patient's actual heart condition. Without them, it would be more difficult for the system operator to derermine the cause of an unusual ECG signal.

We claim:

1. In an electrocardiac telemetry system having a receiver and a transmitter which transmits to the receiver a carrier signal that is modulated by a subcarrier that is modulated by electrocardiac signals applied to the transmitter from electrodes that are attached to a patient, apparatus for producing an indication that an electrode is detached from the patient comprises:

circuit means in the transmitter coupled to the electrodes for producing a control signal in response to the open circuit condition of an electrode detached from a patient;

a signal-controlled source of subcarrier signal in the transmitter having first and second subcarrier operating frequencies;

means coupled to said source for applying electrocardiac signals thereto to modulate the operating frequency thereof about the first subcarrier frequency in response to applied electrocardiac signal;

means coupling said circuit means to said source for altering the operating frequency thereof to the second subcarrier frequency in response to control signal applied thereto from said circuit means;

carrier signal generating means coupled to said source for transmitting a carrier signal modulated by said subcarrier signal;

receiver means including a detector responsive to transmitted carrier signal modulated at said second subcarrier frequency received by the receiver means for producing an output that is indicative of electrode detachment from a patient.

2. In an electrocardiac telemetry system having a receiver and a transmitter which transmits to the receiver a carrier signal that is modulated by a subcarrier that is modulated by electrocardiac signals applied to the transmitter from electrodes that are attached to a patient, the method of producing an indication that an electrode is detached from the patient, comprising the steps of:

detecting the open circuit condition of an electrode detached from a patient;

altering the frequency of the subcarrier in the transmitter form one frequency to another frequency in response to detection of a detached electrode;
sensing the altered subcarrier frequency at the receiver; and providing an indication of inoperative condition in response to the altered subcarrier frequency received at the receiver.

* * * * *